(12) United States Patent
Ueno et al.

(10) Patent No.: US 6,530,918 B1
(45) Date of Patent: Mar. 11, 2003

(54) LASER TREATMENT APPARATUS

(75) Inventors: Tokio Ueno, Nagoya (JP); Seiki Tomita, Gamagori (JP)

(73) Assignee: Nidek Co., LTD, Gamagori (JP)

( * ) Notice: Subject to any disclaimer, the term of this patent is extended or adjusted under 35 U.S.C. 154(b) by 0 days.

(21) Appl. No.: 09/668,151

(22) Filed: Sep. 25, 2000

(30) Foreign Application Priority Data

Sep. 27, 1999 (JP) .......................................... 11-271996

(51) Int. Cl.⁷ .............................................. A61B 18/20
(52) U.S. Cl. .............................. 606/10; 606/4; 606/11; 607/89
(58) Field of Search ...................... 607/88–95; 606/4, 606/6, 10–11, 16–18

(56) References Cited

U.S. PATENT DOCUMENTS

| | | | | |
|---|---|---|---|---|
| 3,769,963 A | * | 11/1973 | Goldman et al. | 219/121.63 |
| 4,289,378 A | * | 9/1981 | Remy et al. | 219/121.76 |
| 4,573,465 A | | 3/1986 | Sugiyama et al. | |
| 4,580,559 A | * | 4/1986 | L'Esperance | 351/217 |
| 5,219,347 A | * | 6/1993 | Negus et al. | 606/17 |
| 5,252,999 A | | 10/1993 | Sukigara et al. | |
| 5,540,676 A | * | 7/1996 | Freiberg | 606/10 |
| 5,601,738 A | | 2/1997 | Engelhardt et al. | |
| 5,954,711 A | | 9/1999 | Ozaki et al. | |
| 6,033,396 A | * | 3/2000 | Huang et al. | 606/10 |
| 6,269,818 B1 | * | 8/2001 | Lui et al. | 128/898 |
| 6,290,714 B1 | * | 9/2001 | Streeter | 606/10 |

FOREIGN PATENT DOCUMENTS

| | | |
|---|---|---|
| EP | 0 624 422 | 11/1994 |
| EP | 0 960 610 A1 | 12/1999 |
| JP | 2000-185072 | 7/2000 |

* cited by examiner

*Primary Examiner*—Lee Cohen
*Assistant Examiner*—Henry M. Johnson, III
(74) *Attorney, Agent, or Firm*—Oliff & Berridge, PLC

(57) ABSTRACT

A laser treatment apparatus for irradiating an affected part of a patient with a treatment laser beam to treat the affected part is disclosed. The apparatus includes a treatment laser beam irradiation system for emitting and delivering the treatment laser beam of a wavelength in a visible region to irradiate the affected part; an observation system provided with an observation optical system for observing the affected part; a protective filter disposed in an optical path of the observation optical system, for intercepting the treatment beam; a first aiming beam irradiation system for emitting and delivering a first aiming beam of about the same wavelength as the wavelength of the treatment beam to irradiate the affected part; a second aiming beam irradiation system for emitting and delivering a second aiming beam of a different wavelength in a visible region from the wavelength of the treatment beam to irradiate the affected part; and an aiming beam switching system for switching between irradiation of the first aiming beam and irradiation of the second aiming beam.

11 Claims, 5 Drawing Sheets

LASER TREATMENT APPARATUS

BACKGROUND OF THE INVENTION

1. Field of the Invention

The present invention relates to a laser treatment apparatus for irradiating an affected part of a patient with a treatment laser beam to treat the affected part.

2. Description of Related Art

There have been used laser treatment apparatus such as a photocoagulation device for irradiating an affected part of an eye fundus of a patient with a treatment laser beam (hereinafter simply referred to as a treatment beam) to coagulate the affected part by heat for treatment. In irradiation of the treatment beam to the eye fundus, such the apparatus is operated by an operator, who observes the patient's eye with a slit lamp, to perform sighting (aiming) of the treatment beam to a desired site on the affected part by utilizing an aiming laser beam (hereinafter simply referred to as an aiming beam) made coaxial with the treatment beam. When the aiming beam and the treatment beam are different in color (wavelength), which causes refraction and dispersion differences based on the wavelength differences, the difference may possibly occur in reaching conditions to the eye fundus between the beams of different colors (wavelengths). For preventing this problem, it is preferable to use the aiming beam of the same color as the color of the treatment beam.

In the laser treatment apparatus, normally, a protective filter is interposed in an optical path for observation in the slit lamp in order to cut or intercept the treatment beam reflected by the patient's eye and others to protect the eyes of an operator during the treatment beam irradiation. Accordingly, if the aiming beam of the same color as that of the treatment beam is used, the aiming beam is also cut or intercepted by the protective filter, so that the aiming beam becomes invisible. As a result, the irradiation site of the aiming beam, namely, of the treatment beam could not be visually recognized by the operator during the treatment beam irradiation.

SUMMARY OF THE INVENTION

The present invention has been made in view of the above circumstances and has an object to overcome the above problems and to provide a laser treatment apparatus which enables an operator to recognize an irradiation site with a treatment beam during irradiation even if using an aiming beam having the same color (wavelength) as that of the treatment beam.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for irradiating an affected part of a patient with a treatment laser beam to treat the affected part, the apparatus including: treatment laser beam irradiation means for emitting and delivering the treatment laser beam of a wavelength in a visible region to irradiate the affected part; observation means provided with an observation optical system for observing the affected part; a protective filter disposed in an optical path of the observation optical system, for intercepting the treatment beam; first aiming beam irradiation means for emitting and delivering a first aiming beam of about the same wavelength as the wavelength of the treatment beam to irradiate the affected part; second aiming beam irradiation means for emitting and delivering a second aiming beam of a different wavelength in a visible region from the wavelength of the treatment beam to irradiate the affected part; and aiming beam switching means for switching between irradiation of the first aiming beam and irradiation of the second aiming beam.

Preferably, the laser treatment apparatus further includes trigger means for generating a trigger signal to instruct irradiation of the treatment beam, wherein the aiming beam switching means switches between irradiation of the first aiming beam and irradiation of the second aiming beam in accordance with a presence or absence of the trigger signal from the trigger means.

Preferably, the laser treatment apparatus further including filter detection means for detecting whether the protective filter is in the optical path of the observation optical system, wherein the aiming beam switching means switches between irradiation of the first aiming beam and irradiation of the second aiming beam in accordance with a detection result of the filter detection means.

Preferably the laser treatment apparatus further including: trigger means for generating a trigger signal to instruct irradiation of the treatment beam; filter moving means for inserting or retracting the protective filter in or from the optical path of the observation optical system; and control means for controlling the filter moving means in accordance with a presence or absence of the trigger signal from the trigger means.

In the laser treatment apparatus, preferably, the aiming beam switching means switches between irradiation of the first aiming beam and irradiation of the second aiming beam in accordance with a type of an insertion/retraction driving mechanism of the protective filter.

In the laser treatment apparatus, preferably, the first aiming beam irradiation means includes attenuation means for attenuating output power of the treatment laser beam, the treatment laser beam with the attenuated output power being irradiated as the first aiming beam to the affected part.

In the laser treatment apparatus, preferably, the attenuation means includes a filter for attenuating the output power of the treatment beam to 1/100 to 1/1000.

According to another aspect of the present invention, there is provided a laser treatment apparatus for irradiating an affected part of a patient with a treatment laser beam to treat the affected part, the apparatus including: a treatment beam irradiation optical system provided with a first laser source for emitting the treatment laser beam of a wavelength in a visible region, for delivering the treatment beam to irradiate the affected part; an observation optical system for observing the affected part; a protective filter disposed in an optical path of the observation optical system, for intercepting the treatment beam; a first aiming beam irradiation optical system for emitting and delivering a first aiming beam of about the same wavelength as that of the treatment beam to irradiate the affected part; a second aiming beam irradiation optical system provided with a second laser source for emitting a second aiming beam of a different wavelength in the visible region from the wavelength of the treatment beam, for delivering the second aiming beam to irradiate the affected part; and a control unit for switching between irradiation of the first aiming beam and irradiation of the second aiming beam.

In the laser treatment apparatus, preferably, the first aiming beam irradiation optical system includes attenuation means for attenuating output power of the treatment laser beam emitted from the first laser source, and the attenuated treatment laser beam being used as the first aiming beam.

In the laser treatment apparatus, preferably, the attenuation means includes a filter for attenuating the output power of the treatment laser beam to 1/100 to 1/1000.

In the laser treatment apparatus, preferably, the control unit controls the first laser source, the second laser source and the attenuation means individually to switch between irradiation of the first aiming beam and irradiation of the second aiming beam.

Preferably, the laser treatment apparatus further including a trigger switch for generating a trigger signal to instruct irradiation of the treatment laser beam, wherein the control unit switches irradiation of the first aiming beam and irradiation of the second aiming beam in accordance with a presence or absence of the trigger signal.

Preferably, the laser treatment apparatus further including a sensor for detecting whether the protective filter is in the optical path of the observation optical system, wherein the control unit switches between irradiation of the first aiming beam and irradiation of the second aiming beam in accordance with a detection result of the sensor.

Preferably, the laser treatment apparatus further including: a trigger switch for generating a trigger signal to instruct irradiation of the treatment laser beam; and a filter moving unit for inserting/retracting the protective filter in/from the optical path of the observation optical system; wherein the control unit controls the filter moving unit in accordance with a presence or absence of the trigger signal.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of a preferred embodiment of a laser treatment apparatus embodying the present invention will now be given referring to the accompanying drawings.

Figure 1:
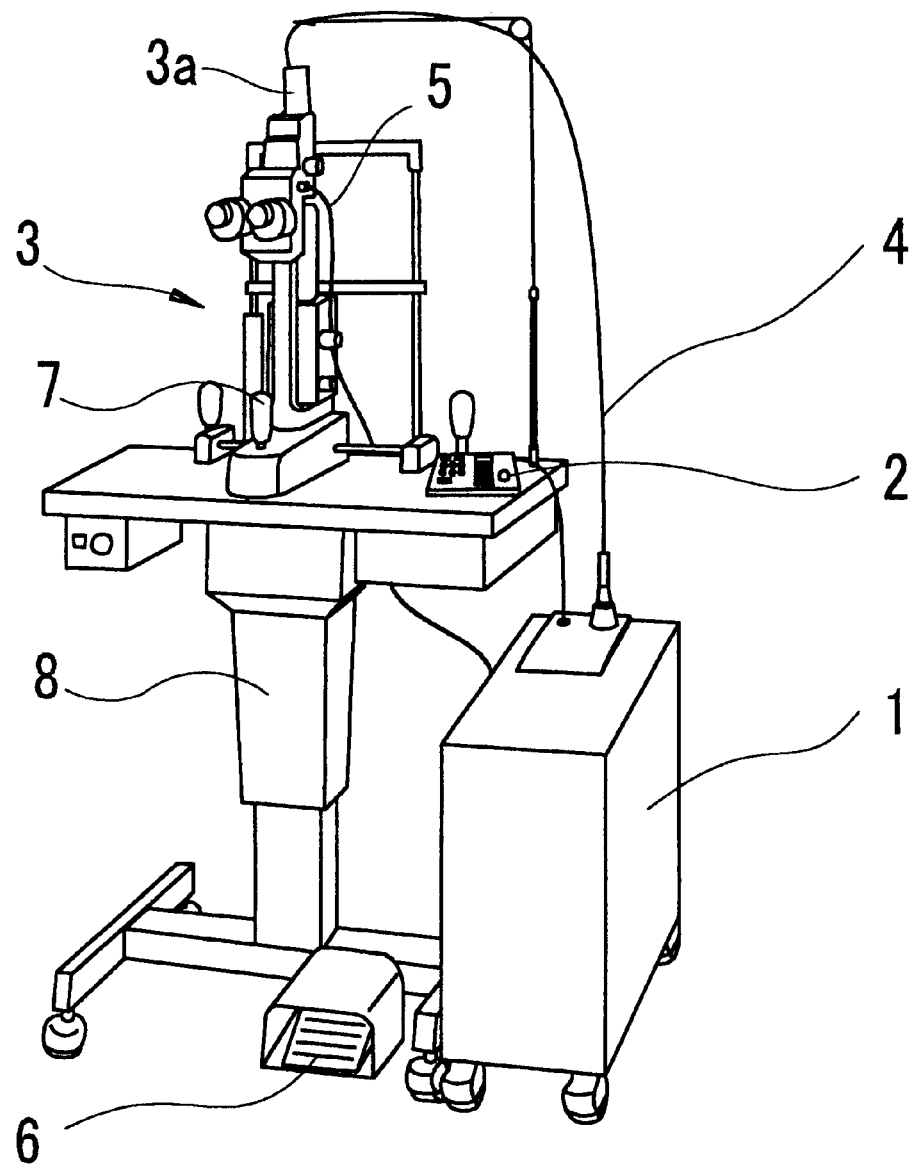
FIG. 1 is a schematic perspective view of a laser treatment apparatus in an embodiment according to the present invention.
Figure 2:
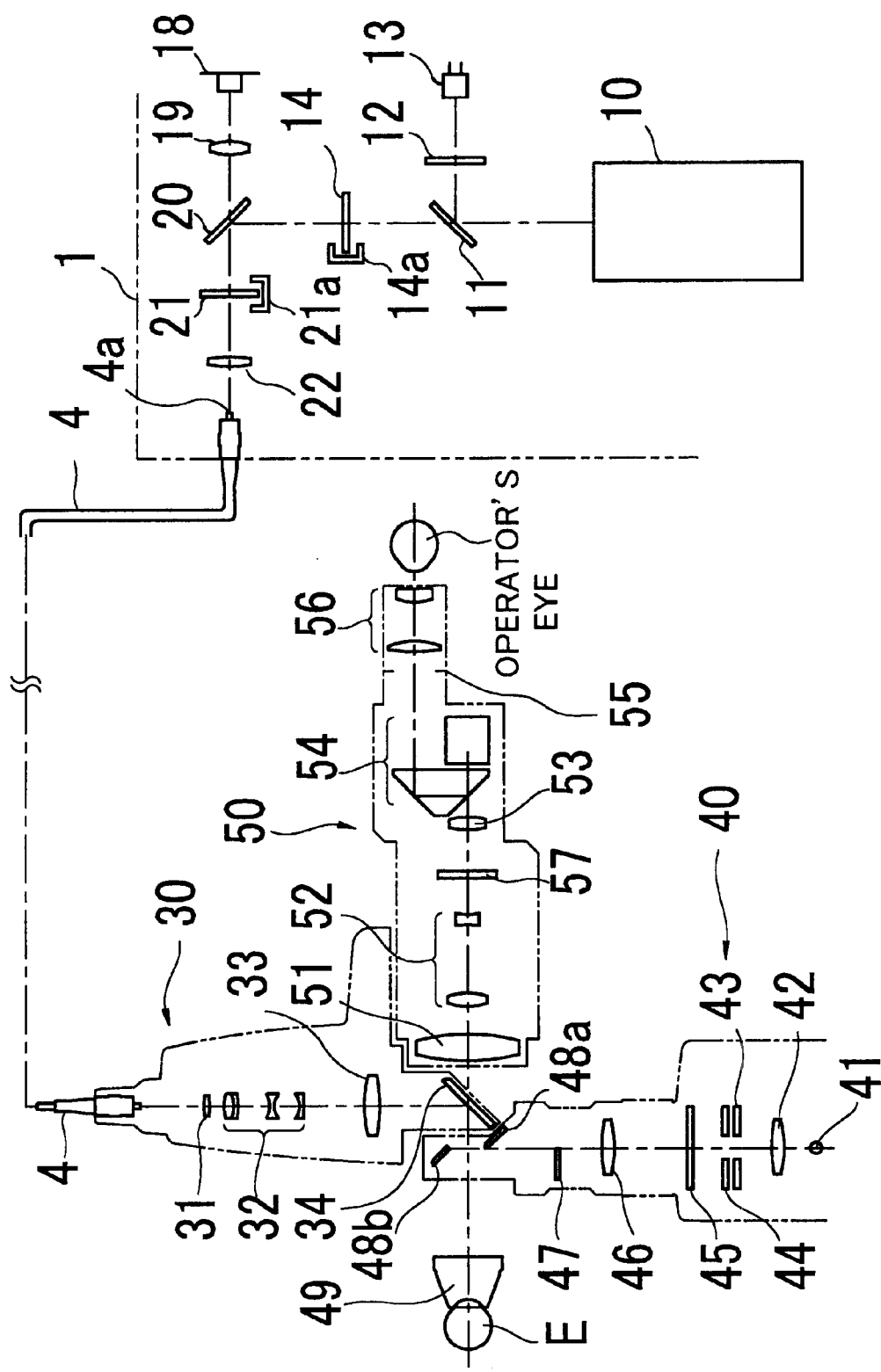
FIG. 2 is a schematic structural view of an optical system of the apparatus in the embodiment.
Figure 3:
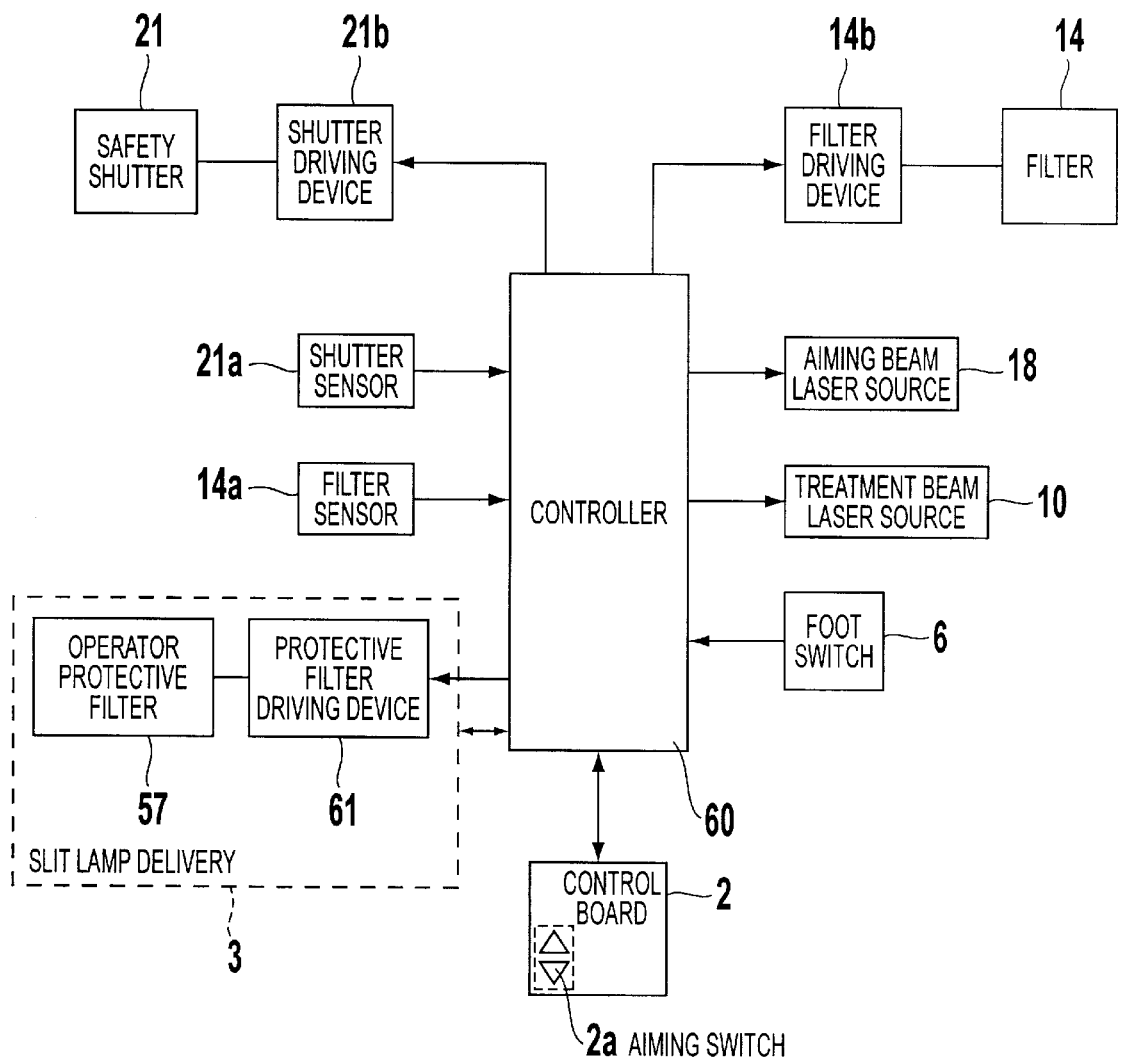
FIG. 3 is a schematic block diagram of a main part of a control system of the apparatus in the embodiment.

FIG. 1 is a schematic perspective view of the laser treatment apparatus in the present embodiment; FIG. 2 is a schematic structural view of an optical system of the apparatus; and FIG. 3 is a schematic block diagram of a main part of a control system of the apparatus.

Numeral 1 is a main unit of the laser treatment apparatus. Numeral 2 is a control board for inputting settings such as irradiation conditions of a treatment laser beam (hereinafter simply referred to as a treatment beam) and light quantity of an aiming laser beam (hereinafter simply referred to as an aiming beam), etc. Numeral 3 is a slit lamp delivery internally provided with an illumination optical system 40 and an observation optical system 50. The slit lamp delivery 3 is provided at its head with an irradiation section 3a including an irradiation optical system 30 for delivering the treatment beam and the aiming beam from the main unit 1 to irradiate an eye of a patient. Numeral 4 is an optical fiber cable for delivering the treatment beam and the aiming beam from the main unit 1 to the irradiation section 3a.

Numeral 5 is a multi-conductor cable used for transmission/reception of signals of various kinds between the slit lamp delivery 3 and the main unit 1. Numeral 6 is a footswitch for generating a trigger signal to start the irradiation of the treatment beam. Numeral 7 is a joystick for moving the slit lamp delivery 3 on a table of a base stand 8.

Numeral 10 is a laser source which emits the treatment beam.

In the present embodiment, an Nd:YAG laser capable of oscillating a fundamental wavelength of 1064 nm is used to generate a green light of 532 nm (linearly polarized light) which is double the fundamental wavelength. Numeral 11 is a beam splitter for transmitting most of the treatment beam from the laser source 10 while reflecting a part thereof. The treatment beam reflected by the beam splitter 11 is incident to a power sensor 13 through a diffusing plate 12. The power sensor 13 detects the output power of the treatment beam emitted from the laser source 10.

Numeral 14 is a filter for largely attenuating the power of the green light (treatment beam) emitted from the laser source 10 so that the attenuated light is used as the aiming beam having the same color (wavelength) (hereinafter referred to as the same-color aiming beam) as that of the treatment beam. When the filter 14 is moved out of the optical path by means of a filter driving device 14b, the green light (treatment beam) emitted from the laser source 10 without attenuation is used for the treatment beam. It is to be noted that a sensor 14a detects the open/close (insertion/retraction) state of the filter 14.

Numeral 18 is a laser source which emits an aiming beam. In the present embodiment, the laser source 18 is a laser diode capable of emitting a red light having a wavelength of 630 nm. It is to be noted that the aiming beam is not limited to the red light of 630 nm. Any light may be adopted if only it differs in color (wavelength) from the treatment beam emitted from the laser source 10 and it is not intercepted by an operator protective filter 57 (mentioned later) disposed in the observation optical system 50. The aiming beam (hereinafter referred to as the different-color aiming beam) emitted from the laser source 18 passes through a collimator lens 19 and it is made coaxial with the treatment beam by a dichroic mirror 20.

Numeral 21 is a safety shutter which is inserted in or retracted from the optical path by a shutter driving device 21b. The open/close (insertion/retraction) state of this shutter 21 is detected by a sensor 21a. Numeral 22 is a condensing lens for condensing the treatment beam and the aiming beam into an entrance end 4a of the fiber 4. The laser beams are delivered through the fiber 4 to the irradiation optical system 30 of the slit lamp delivery 3.

The irradiation optical system 30 is constructed of a collimator lens 31, a group of variable magnification lenses 32, an objective lens 33, and a driven mirror 34. The variable magnification lens 32 is moved along the optical axis with the turn of a knob not shown to thereby change each spot diameter of the laser beams. The driven mirror 34 can freely change its reflecting angle with the control of a manipulator not shown by the operator.

The illumination optical system 40 is provided with a light source 41 which emits a visible illumination light, a condensing lens 42, a variable circular aperture 43, a variable slit plate 44, a filter 45, a projection lens 46, a correcting lens 47, and splitting mirrors 48a and 48b. The aperture 43 and the slit plate 44 are used for determining the height and width of the illumination light to form luminous flux in a slit form. Numeral 49 is a contact lens for laser treatment, which is placed on a patient's eye E in the treatment.

The observation optical system 50 is constructed of an objective lens 51 used in common between a right and left observation optical paths and two sets each including a group of variable magnification lenses 52, an image forming lens 53, an erect prism 54, a field diaphragm 55, a group of eyepiece lenses 56, and a protective filter 57 used for protecting the eyes of the operator from the treatment beam reflected by the patient's eye E and the contact lens 49. Each set of the components 52–57 is disposed on the right and left optical paths respectively.

As the protective filter 57, there are for example a fixed type which is always placed on the observation optical path, a hand-operated type which is manually inserted in or retracted from the observation optical path, and an electrically operated type which is automatically inserted in or retracted from the observation optical path in response to the trigger signal from the footswitch 6. In the present embodiment, the protective filter 57 is of an electrically operated type which is automatically inserted in or retracted from the observation optical path by means of a filter driving device 61 which is filter moving means of the present invention. The protective filters 57 are placed out of the respective observation optical paths during observation of the eye E. Upon receipt of the trigger signal from the footswitch 6 acting as a trigger of the treatment beam irradiation, a controller 60 drives the filter driving device 61 to insert the protective filters 57 in the respective optical paths. Alternatively, a switch for inserting or retracting the protective filters 57 may be provided. In this case, the filter driving device 61 is driven in response to the signal from the switch.

Figure 4:
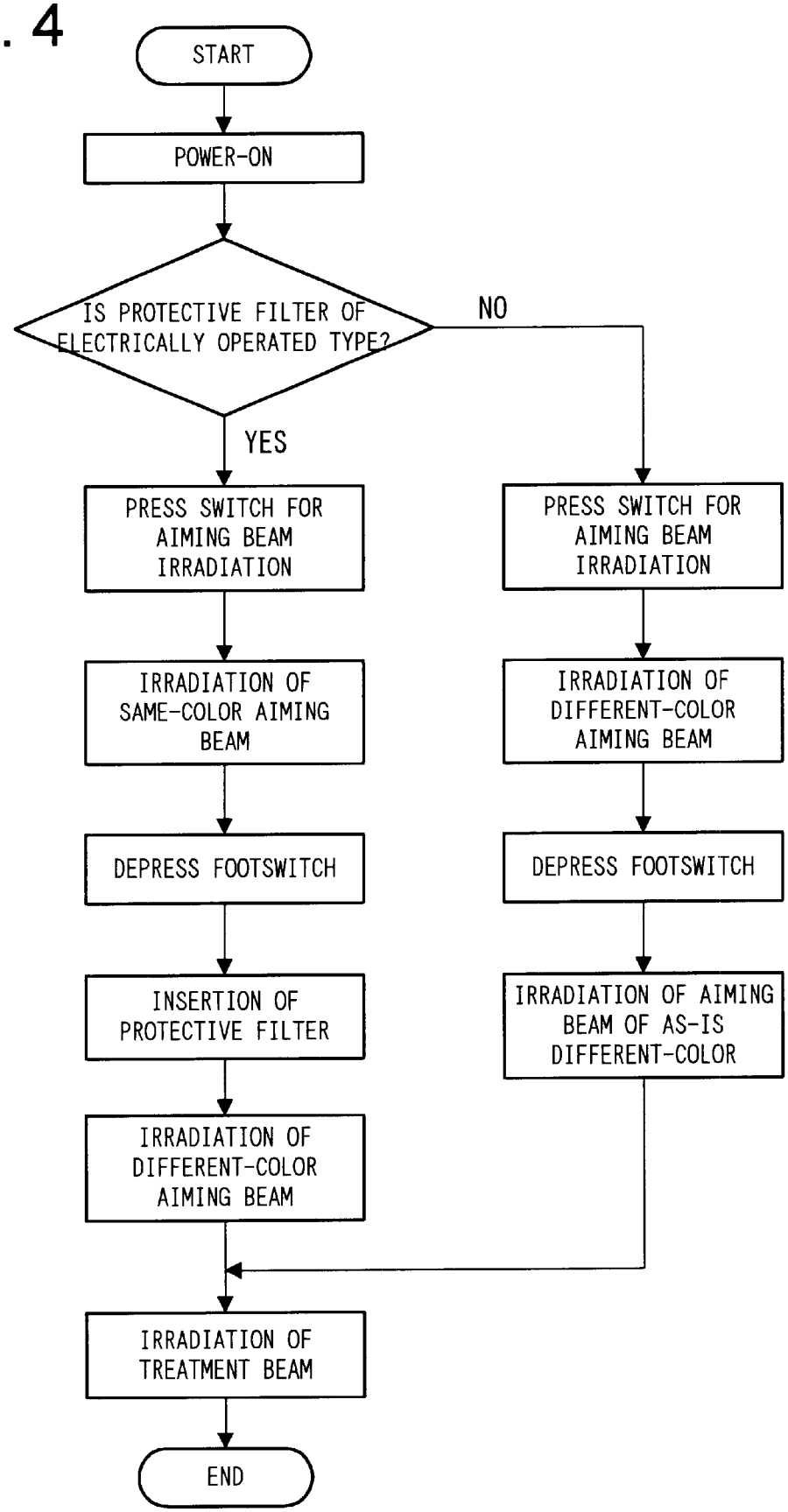
FIG. 4 is a flowchart of an irradiation control of an aiming beam.

Operation of the apparatus constructed as above will be explained below, referring to FIG. 4.

Upon power-on of the main unit 1, the controller 60 determines the type of an insertion/retraction driving mechanism of the protective filter 57 among the fixed type, the hand-operated type, or the electrically-operated type, based on an identifying signal from the slit lamp delivery 3 side. In the present embodiment, the protective filter 57 is of the electrically operated type.

Prior to execution of the laser treatment, the operator presses an aiming switch 2a provided on the control board 2 to provide the aiming beam, and observes the fundus of the eye E through the observation optical system 50, the eye E being illuminated by the illumination light from the illumination optical system 40. At this time, since the protective filter 57 has an electrically driven mechanism in the present embodiment, the controller 60 judges that the same-color aiming beam should be emitted. The controller 60 therefore drives the laser source 10 to emit the treatment beam, whereby to make the treatment beam pass through the filter 14. By the passage of the treatment beam through the filter 14, the output power of the treatment beam is attenuated to about 1/100 to 1/1000 of a standard power. The power attenuated treatment beam is used as the aiming beam. Thus the aiming beam of the same color (wavelength) as that of the treatment beam can be provided. When such same-color aiming beam is emitted, the controller 60 controls the shutter driving device 21b to move the shutter 21 out of the optical path.

The operator observes the same-color aiming beam applied to the eye fundus and controls the joystick 7 and the manipulator not shown to perform the sighting (alignment) to the affected part. Then, the operator inputs the irradiation conditions including the irradiation power and the irradiation time of the treatment beam with the switches on the control board 2. It is to be noted that the irradiation conditions may be set in advance.

After preparation for the irradiation of the treatment beam, the operator operates the manipulator to fine adjust the sighting using the same-color aiming beam to the affected part. After completion of the sighting, the operator depresses the footswitch 6, thereby starting the irradiation of the treatment beam.

The controller 60, upon receipt of the trigger signal from the footswitch 6, causes the laser source 18 to emit the different-color aiming beam and, simultaneously, drives the filter driving device 61 to insert the protective filters 57 in the respective optical paths. Subsequently, the controller 60 controls the laser source 10 to emit the treatment beam at the predetermined irradiation power set with the use of the control board 2. When the sensor 13 detects the predetermined irradiation power, the controller 60 moves the filter 14 to the outside of the optical path.

The treatment beam and the different-color aiming beam are delivered through the fiber 4 and the irradiation optical system 30 to the affected part of the eye E to irradiate the affected part of the eye E. This aiming beam being different in color from the treatment beam, the operator can recognize the aiming beam even though the protective filter 57 is disposed in the observation optical path (or even during the irradiation of the treatment beam). Accordingly, the operator can also recognize the irradiation site of the treatment beam.

Figure 5:
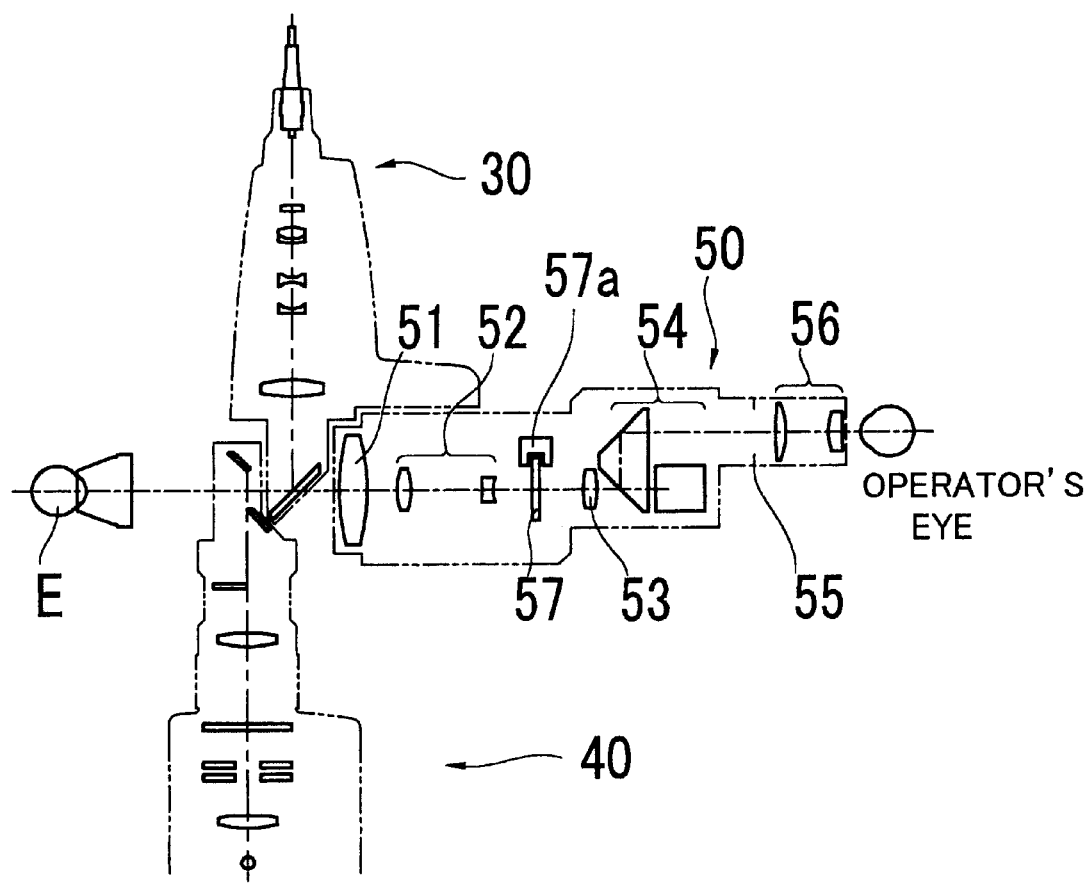
FIG. 5 is a schematic structural view of a modification of a main part of the optical system of the apparatus.

In the above explanation, the ON/OFF state of the footswitch 6 is used for switching between the same-color aiming beam and the different-color aiming beam. Alternatively, a sensor 57a for detecting the insertion/retraction of the protective filter 57 in/from the observation optical path may be provided as shown in FIG. 5. In this case, the switching between the aiming beams differing in color is performed based on a detection result of the sensor 57a.

The electrically operated protective filter 57 is provided in the observation optical system 50 of the slit lamp delivery 3 in the present embodiment. Instead of the electrically operated type, however, there may be cases where the filter 57 of a fixed or hand-operated type is used in a laser treatment apparatus constructed such that the irradiation section 3a is incorporated in an existing slit lamp or a binocular inverted-image mirror which is attached on the head of the operator at the time of use. In using such the apparatus (the inverted-image mirror or the slit lamp), the type of the insertion/retraction mechanism of the protective filter 57 can be determined in advance under the filter identifying signal. In the case of the fixed or hand-operated type, therefore, the controller 60 operates to emit the different-color aiming beam from the beginning (see FIG. 4), instead of emitting the same-aiming beam. As a result, even if the protective filter 57 is interposed in the observation optical path during the observation as well as during the treatment beam irradiation, the different-color aiming beam not intercepted by the protective filter 57 makes it possible for the operator to recognize the irradiation site of the aiming beam.

It is to be noted that in the case of the hand-operated type, the sensor 57a shown in FIG. 5 may be used to detect the insertion/retraction, or presence/absence of the protective filter 57. In this case, at the time when the protective filter 57 is inserted in the optical path, the switching from the same-color aiming beam to the different-color aiming beam is executed.

The switching from the irradiation of the same-color aiming beam to the irradiation of the different-color is not limited to the above manners. A special switch for switching between the aiming beams may be provided in the main unit 1, whereby to permit the switching in accordance with operator's own judgement.

In the above embodiment, the same-color aiming beam is produced as a result of attenuation of the power of the treatment beam emitted from a single laser source. Alternatively, the apparatus may additionally be provided with a laser source specifically designed for emitting an aiming beam of about the same color (wavelength) as that of the treatment beam.

As described above, the laser treatment apparatus in the present embodiment is arranged to appropriately use the aiming beam of the same-color (wavelength) as that of the treatment and the other aiming beam of the different-color. Accordingly, the sighting can be performed with the use of the aiming beam of about the same color as that of the treatment beam at the observation (at nonuse of the protective filter 57). The irradiation site of the treatment beam can be recognized even during the irradiation of the treatment beam (during use of the protective filter 57).

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for irradiating an affected part of a patient with a treatment laser beam to treat the affected part, the apparatus including:

treatment beam irradiation means for emitting and delivering the treatment laser beam of a first wavelength in a visible region to irradiate the affected part;

observation means provided with an observation optical system for observing the affected part;

a protective filter disposed in an optical path of the observation optical system, for intercepting the first wavelength;

attenuation means for attenuating output power of the treatment laser beam, the treatment laser beam with the attenuated output power being irradiated as a first aiming beam to the affected part;

aiming beam irradiation means for emitting and delivering a second aiming beam to irradiate the affected part, the second aiming beam being of a different second wavelength in the visible region from the first wavelength, the second wavelength not being intercepted by the protective filter; and aiming beam switching means for switching between irradiation of the first aiming beam and irradiation of the second aiming beam selectively such that the first aiming beam is irradiated when the treatment beam is not irradiated and the second aiming beam is irradiated when the treatment beam is irradiated.

2. The laser treatment apparatus according to claim 1 further including trigger means for inputting a trigger signal to instruct irradiation of the treatment beam, wherein the aiming beam switching means switches between irradiation of the first aiming beam and irradiation of the second aiming beam selectively in accordance with input of the trigger signal such that the first aiming beam is irradiated when the trigger signal is not input and the second aiming beam is irradiated when the trigger signal is input from the trigger means.

3. The laser treatment apparatus according to claim 1 further including filter detection means for detecting whether the protective filter is in the optical path of the observation optical system, wherein the aiming beam switching means switches between irradiation of the first aiming beam and irradiation of the second aiming beam selectively in accordance with a detection result of the filter detection means such that the first aiming beam is irradiated when the filter is not in the optical path and the second aiming beam is irradiated when the filter is in the optical path.

4. The laser treatment apparatus according to claim 3 further including:

trigger means for inputting a trigger signal to instruct irradiation of the treatment beam;

filter moving means for moving the protective filter in or out of the optical path of the observation optical system; and control means for controlling the filter moving means in accordance with input of the trigger signal from the trigger means.

5. The laser treatment apparatus according to claim 1, wherein the attenuation means includes a filter for attenuating the output power of the treatment beam to 1/100 to 1/1000.

6. A laser treatment apparatus for irradiating an affected part of a patient with a treatment laser beam to treat the affected part, the apparatus including:

treatment beam irradiation means for emitting and delivering the treatment laser beam of a wavelength in a visible region to irradiate the affected part;

observation means provided with an observation optical system for observing the affected part;

a protective filter disposed in an optical path of the observation optical system, for intercepting the wavelength of the treatment beam;

first aiming beam irradiation means for emitting a first aiming beam of a wavelength in the visible region, for delivering the first aiming beam to irradiate the affected part, the wavelength of the first aiming beam being intercepted by the protective filter;

second aiming beam irradiation means for emitting a second aiming beam of a wavelength in the visible region, for delivering the second aiming beam to irradiate the affected part, the wavelength of the second aiming beam not being intercepted by the protective filter;

filter type determining means for determining a type of the protective filter between a movable type and a fixed type, the movable type of the filter being inserted into and retracted from the optical path, the fixed type of the filter being fixed in the optical path; and aiming beam switching means for switching between irradiation of the first aiming beam and irradiation of the second aiming beam selectively in accordance with a determination result of the filter type determination means such that the second aiming beam is only irradiated when the fixed type is determined and the first and second aiming beams are selectively irradiated when the movable type is determined.

7. A laser treatment apparatus for irradiating an affected part of a patient with a treatment laser beam to treat the affected part, the apparatus including:

a treatment beam irradiation optical system provided with a laser source for emitting the treatment laser beam of a wavelength in a visible region, for delivering the treatment beam to irradiate the affected part;

an observation optical system for observing the affected part;

a protective filter disposed in an optical path of the observation optical system, for intercepting the wavelength of the treatment beam;

a first aiming beam irradiation optical system for emitting a first aiming beam of a wavelength in the visible region, for delivering the first aiming beam to irradiate the affected part, the wavelength of the first aiming beam being intercepted by the protective filter;

a second aiming beam irradiation optical system for emitting a second aiming beam of a wavelength in the visible region, for delivering the second aiming beam to irradiate the affected part, the wavelength of the second aiming beam not being intercepted by the protective filter; and a control unit for switching between irradiation of the first aiming beam and irradiation of the second aiming beam selectively such that the first aiming beam is irradiated when the treatment beam is not irradiated and the second aiming beam is irradiated when the treatment beam is irradiated.

8. The laser treatment apparatus according to claim 7 further including a trigger switch for inputting a trigger signal to instruct irradiation of the treatment laser beam, wherein the control unit switches irradiation of the first aiming beam and irradiation of the second aiming beam selectively in accordance with input of the trigger signal such that the first aiming beam is irradiated when the trigger signal is not input and the second aiming beam is irradiated when the trigger signal is input.

9. The laser treatment apparatus according to claim 7 further including a sensor for detecting whether the protective filter is in the optical path of the observation optical system, wherein the control unit switches between irradiation of the first aiming beam and irradiation of the second aiming beam selectively in accordance with a detection result of the sensor such that the first aiming beam is irradiated when the filter is not in the optical path and the second aiming beam is irradiated when the filter is in the optical path.

10. The laser treatment apparatus according to claim 9 further including:

a trigger switch for inputting a trigger signal to instruct irradiation of the treatment laser beam; and a filter moving unit for inserting or retracting the protective filter in or from the optical path of the observation optical system;

wherein the control unit controls the filter moving unit in accordance with input of the trigger signal.

11. The laser treatment apparatus according to claim 7, wherein the wavelength of the treatment beam and the wavelength of the first aiming beam are approximately the same wavelength.

* * * * *